United States Patent [19]
Carroll

[11] Patent Number: 6,054,705
[45] Date of Patent: Apr. 25, 2000

[54] CHARGE-INTEGRATING PREAMPLIFIER FOR CAPACITIVE TRANSDUCER

[76] Inventor: Lewis Carroll, 3130 Lewiston Ave., Berkeley, Calif. 94705

[21] Appl. No.: 08/834,089

[22] Filed: Apr. 14, 1997

Related U.S. Application Data

[63] Continuation-in-part of application No. 08/726,849, Oct. 4, 1996, abandoned, which is a continuation-in-part of application No. 08/407,687, Mar. 20, 1995, abandoned.

[51] Int. Cl.$^7$ .................................................... H01J 40/14
[52] U.S. Cl. ............................... 250/214 A; 250/214 LA; 330/308
[58] Field of Search ........................ 250/214 A, 214 LA, 250/214 AG, 370.01, 370.09, 214.1, 214 R; 330/308, 309, 278, 279; 327/514, 342–345

[56] References Cited

U.S. PATENT DOCUMENTS

| | | | |
|---|---|---|---|
| 3,218,462 | 11/1965 | Raub et al. | 330/308 |
| 3,713,031 | 1/1973 | Williams et al. | 330/16 |
| 4,535,233 | 8/1985 | Abraham | 250/214 A |
| 4,638,152 | 1/1987 | Takada | 250/214 A |
| 4,647,762 | 3/1987 | Chown | 250/214 A |
| 4,888,562 | 12/1989 | Edler | 330/308 |
| 5,194,736 | 3/1993 | Meulenbrugge et al. | 250/370.09 |
| 5,322,995 | 6/1994 | Ohkawa et al. | 250/214 A |
| 5,448,056 | 9/1995 | Tsuruta | 250/214 A |

OTHER PUBLICATIONS

Section 3.8 in Designing with Field Effect Transistors Siliconix, Inc. revised by Ed Oxner, 2nd Ed. McGraw–Hill New York pp. 89–92, Jan. 1990.

Silicon Photo Diodes and Charge–Sensitive Amplifiers for Scintillation Counting and High–Energy Physics. Hamamatsu Photonics K.K. Solid State Division Cat #KOTH0002E02 Jun., 1993, pp. 23–27.

"Fet Applications" Application Note AN–32 (Feb., 1970; Revised Jun. 1986) pp. 94–95 in National Semiconductor Linear Applications Handbook, National Semiconductor, Inc. 1994.

*Primary Examiner*—Que T. Le

[57] ABSTRACT

A capacitive transducer which converts impulses of absorbed energy into impulses of electronic charge, combined with a unity-gain, non-inverting amplifier and an integrating capacitor which is substantially smaller than the transducer capacitance, further combined with a transconductance amplifier, comprises a simple and compact radiation detector probe. The detector probe, connected to a signal-receiving assembly through a shielded cable, comprises a useful apparatus for detecting and amplifying weak impulses of energy absorbed from X-ray photons, gamma-ray photons, or nuclear charged particles.

8 Claims, 5 Drawing Sheets

CHARGE-INTEGRATING PREAMPLIFIER FOR CAPACITIVE TRANSDUCER

This is a continuation-in-part of Application Ser. No. 08/726,849, filed Oct. 4, 1996, now abandoned, which, in turn, is a continuation-in-part of application Ser. No. 08/407,687 filed Mar. 20, 1995 (now abandoned).

BACKGROUND

1. Field of Invention

This invention relates to apparatus for detecting and amplifying weak impulses of energy absorbed from incident x-ray photons, gamma ray photons, or nuclear charged particles.

2. Discussion of Prior Art

Semiconductor junction diodes, employed alone or combined with (i.e. optically coupled to) a scintillating crystal, are used as transducers to convert impulses of energy absorbed from incident x-ray photons, gamma ray photons, or nuclear charged particles, into pulses of electronic current. The time-integral of current, or charge (in coulombs), contained in each electronic pulse is a measure of the amount of energy (in joules, or equivalently, in electron-volts) deposited by the corresponding photon or charged particle.

The small-signal, linear-equivalent circuit model of the semi-conductor diode transducers used in these applications is shown conceptually as an idealized, pulsed current source connected in parallel with a capacitor which represents the diode junction capacitance. Depending on specific diode type and its operating (reverse-bias) potential, the junction capacitance can range from a few picofarads to several hundreds of picofarads.

When an X-ray photon, gamma-ray photon, or nuclear charged-particle is absorbed in the transducer, the energy from each impact is converted into a pulse of electronic current. Each pulse of electronic current, in turn, charges the transducer diode-junction capacitance producing a corresponding voltage signal whose amplitude equals the charge in the pulse divided by the diode junction capacitance.

The amount of charge in each transducer current pulse is quite small—on the order of a few femtocoulombs (1 femtocoulomb=$10^{-15}$ coulomb) for low-energy X-ray photons—so that the corresponding voltage pulses are very weak and must be amplified by a factor of 10,000 or more, via several stages of amplification, to enable accurate signal processing, measurement, and analysis.

Applications such as radiation monitoring, dosimetry, and spectroscopy require detection, amplification, counting, measurement, and analysis of the distribution of amplitudes (referred to as "analysis of the pulse-height spectrum") of the electronic pulses produced by the transducer. Detection, counting, measurement, and analysis invariably occur in the presence of perturbing effects, such as thermal noise and electronic "shot" noise in the amplifying circuitry and in the transducer itself. These perturbing effects, in turn, set a lower limit to the magnitude of impulses which can be detected over the noise, and limit, as well, the overall precision of the amplitude-measurement and analysis process.

Figure 1A:
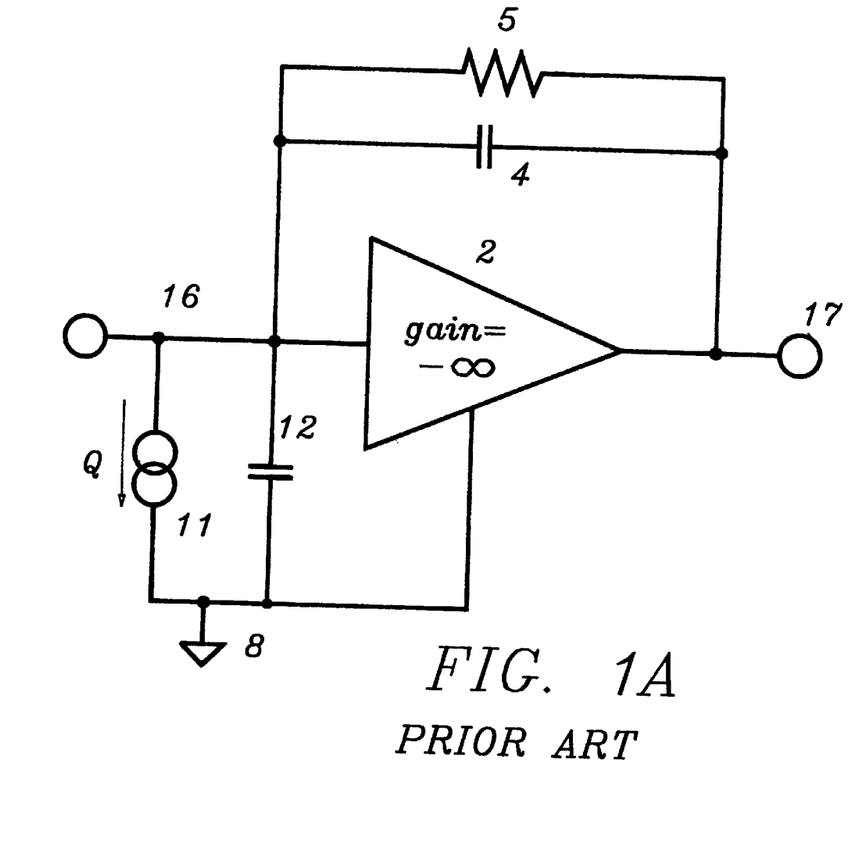
FIG. 1A and 1B are schematic representation illustrating the prior art.
Figure 1B:
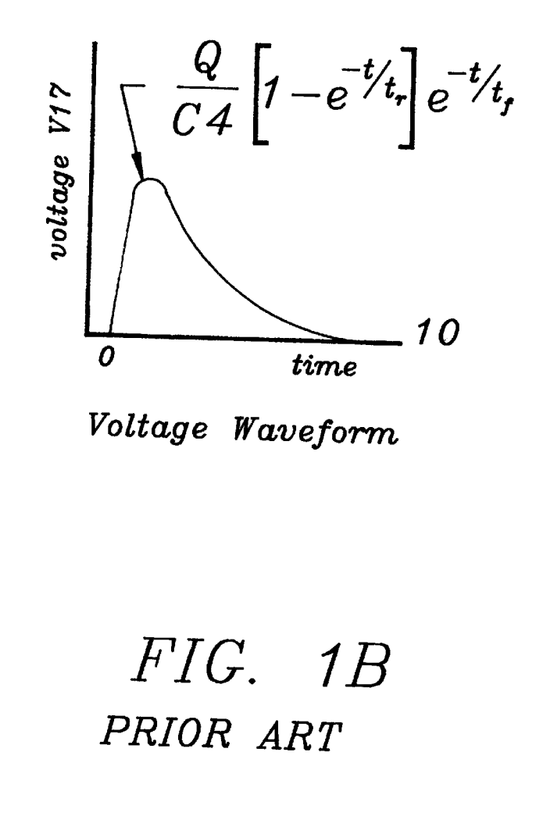

The lower limit of signal detectability and, correspondingly, the highest achievable measurement precision, is a function of various system components and operating parameters such as time constants, bias conditions, ambient temperature, etc. In order to preserve the highest possible signal-to-noise ratio, the first amplifying stage, or "preamplifier", used with a high-impedance, capacitive transducer, is generally configured as a "charge-integrating preamplifier" wherein the transducer, modelled by the parallel connection of pulsed current-source 11 and capacitor 12 shown in FIG. 1, is connected between the inverting input 16 of a high-gain inverting amplifying device 2, and circuit common 8.

A small feedback integrating capacitor 4, whose capacitance is typically of the order of five to ten percent of the transducer capacitance, is connected from the output of the amplifying circuit or device, back to the inverting input.

This configuration exploits the well-known "Miller-Effect" in which the additional parallel capacitance, as "seen" by the transducer, is effectively the value of the feedback capacitor multiplied by the voltage gain of the amplifying device. In the conceptual ideal, the amplifying device has "infinite" voltage gain, so that the additional parallel capacitance seen by the transducer is also "infinite". Thus, essentially all of the charge contained in each impulse of current generated by the transducer is deposited in the feedback capacitor rather than in the transducer capacitor. The voltage-signal amplitude at the output terminal of the preamplifier is given by the charge in each transducer pulse divided by the (actual) capacitance of the feedback capacitor.

As a practical matter, a discharge resistor 5 is connected in parallel with integrating capacitor 4 to prevent indefinite build-up of charge which would otherwise result in eventual saturation and circuit malfunction. A voltage signal V 17 at terminal 17 (shown as waveform 10 in FIG. 1) is approximated by a mathematical expression (referenced to time t=0):

$$V17 = [Q/C4][1 - e^{-t/t_r}][e^{-t/t_f}]$$

where: Q/C4 is the pulse amplitude, $t_r$ is the pulse "rise-time", which is governed by the charge-collection time-constant of the transducer combined with the bandwidth of amplifier 2, $t_f$ is the pulse "fall-time" defined by the time-constant $t_f = R5 \times C4$ The foregoing is a description of the classic charge-integrating pre-amplifier of the prior art, the essential function of which is to cause most of the charge generated by a high-impedance, capacitive transducer to be deposited in an integrating capacitor which is substantially smaller than the transducer capacitance, thereby producing an amplified signal at the output. The preamplifier gain, expressed in units of "output volts per unit transducer charge" is nominally 1/C4.

The amplifying circuit or device in a classic charge-integrating pre-amplifier must be a high-gain, signal-inverting device, having low-noise, and high (essentially infinite) input-impedance. Above all, the amplifying circuit or device must be stable—free from any tendency toward self-oscillation. In order to achieve stable performance, a charge-integrating pre-amplifier of the prior art must be carefully crafted, utilizing premium, often costly components as justified in applications such as high-resolution x-ray and gamma-ray spectroscopy, working in conjunction with high-performance transducers to high standards of precision.

However, for many applications, particularly those applications requiring miniaturization, remote sensing over long distances, low operating voltage and/or very low power consumption, the classic charge-integrating preamplifier configuration of the prior art is too expensive, too bulky, and consumes too much power.

OBJECTS AND ADVANTAGES OF THE INVENTION

Therefore it is an object of the present invention to provide the essential function of the charge-integrating preamplifier of the prior art, producing a stable, low-noise, amplified signal in response to current impulses produced by a capacitive transducer, while replacing the high-gain inverting voltage-amplifier circuit configuration of the prior art with a simple, inexpensive, non-inverting, unity-gain voltage-amplifier, in combination with a transconductance-amplifier and signal-receiver, in a configuration which is well-suited to miniature, low-voltage, low-cost transducers such as silicon PIN diodes.

A further object of the invention is to provide the essential function of the charge-integrating preamplifier of the prior art in an apparatus, incorporating structural elements of the apparatus, such as wiring capacitance and amplifier input capacitance, as part of the charge-integrating capacitance of the apparatus.

Another object of the invention is to combine a novel preamplifier with an appropriate transducer in a miniature probe so as to produce an inexpensive, compact and rugged radiation detector in a configuration suitable for applications such as in-line monitoring and process-control of automated radioisotope labelling and chemical synthesis procedures.

Another object of the invention is combine a novel preamplifier with an appropriate transducer so as to produce a simple, compact, low-cost radiation detector as modular, detachable probe for applications in which the probe may be considered a disposable element.

A further object of the invention is to provide the essential function of the charge-integrating preamplifier of the prior art, but in a low-power implementation for use in remote-sensing or portable, battery-operated, instrumentation applications.

Another object of the invention is to combine a novel pre-amplifier with an appropriate transducer in a miniature probe configuration which can be operated remotely at distances of hundreds of feet, connected to a signal receiver, power source, and additional amplifying stages by means of a single-conductor, shielded coaxial cable.

Other features, advantages, and novel aspects of the invention will become apparent to those skilled in the art from the following specifications and drawings illustrating the underlying concept and examples of practical embodiments.

REFERENCE NUMERALS IN DRAWINGS

2 Idealized, high-gain, inverting, amplifier
3a, 3b Idealized unity-gain, non-inverting, amplifier model
4, 4a, 4b Capacitors with capacitance C4, C4a, C4b respectively
5, 5b Resistors with resistance R5, R5b respectively
6a Input terminal; the voltage at terminal 6a is designated V6a
6b Input terminal; the voltage at terminal 6b is designated V6a
7a Output terminal; voltage at terminal 7a is designated V7a
7b Output terminal; voltage at terminal 7b is designated V7b
8 Signal "common" or "ground" eference
10 Voltage waveform of idealized prior-art preamplifier configuration
10a Voltage waveform of idealized new preamplifier configuration (no discharge resistor)
10b Voltage waveform of idealized new configuration (including discharge resistor)
11, 11a, 11b Pulsed current-source
12, 12a, 12b Capacitor
16 Input terminal of idealized, high-gain, inverting amplifier; the voltage at terminal 16 is designated V16
17 Output terminal of idealized, high-gain, inverting amplifier; the voltage at terminal 17 is designated V17
18 Photon Source
19 X-ray or gamma ray photons
20, 59 High-impedance capacitive transducers: silicon PIN diodes serving as a photon detectors
21 Voltage-controlled amplifing device (JFET) with transconductance=$Gm_{21}$
22 Voltage-controlled amplifying device (JFET) with transconductance=$Gm_{22}$
23, 23', 64 Amplifying device (JFET) source-bias resistors
24, 65 Discharge means—High-megohm Resistors
25 Amplifying device (JFET) signal input (gate) terminal; the voltage at terminal 25 is designated V25
26 Amplifying device (JFET) signal output (source) terminal; the voltage at terminal 26 is designated V26
27 Detector probe power-supply bus
28, 67 Coupling capacitors
29 Transducer bias and signal isolation resistor
30 Metallic shielding enclosure housing detector probe assembly
30' Metallic shielding enclosure housing signal-receiving circuit assembly
32 (+)Voltage power supply
33a, 68a Capacitor representing equivalent input capacitance of amplifier
33b, 68b Capacitor representing wiring capacitance
33c, 68c Fixed capacitor of predetermined value
34 Thin, metallic membrane
41 Load resistor
42, 66 Bypass capacitors
45 Shielded cable
50, 51, 52 PNP bipolar transistors
58 Scintillating crystal
60, 61, 62, 63 Amplifying devices: junction field-effect transistors (JFET's)

DESCRIPTION OF THE INVENTION

The invention comprises a detector probe assembly and a signal-receiving assembly. The detector probe assembly comprises a transducer combined with a novel charge-integrating pre-amplifier driving a transconductance amplifier stage. The current-signal from the transconductance amplifier stage, in turn, is transmitted through a shielded cable to the input of a transimpedance-amplifier contained in the signal-receiving assembly.

Idealized Model (A)

An idealized, abbreviated schematic representation illustrating a fundamental concept at the heart of the invention—a novel charge-integrating preamplifier—is shown in FIGS. 2(A–B). Amplifier 3a has infinite input impedance and zero output impedance. The signal voltage at output terminal 7a is designated V7a; the signal voltage at input terminal 6a is designated V6a. The forward signal gain V7a/V6a for a signal applied to terminal 6a is unity and non-inverting. The reverse gain V6a/V7a for a signal applied to terminal 7a is zero. All signal potentials and impedances are referred to circuit common 8.

The transducer model in FIGS. 2(A–B), comprising pulsed current-source 11a in parallel with capacitor 12a, is connected from terminal 7a to terminal 6a of amplifier 3a. At a particular instant of time (denoted t=0), an impulse of current, with charge=Q' is generated by current source 11a.

Figure 2A:
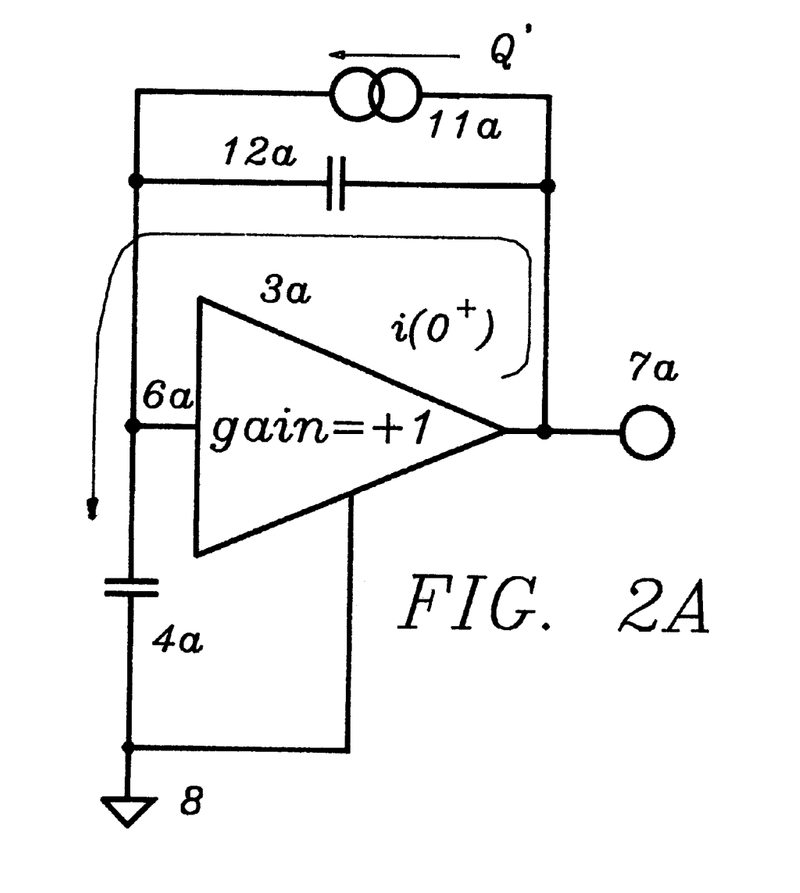
FIG. 2A and 2B are idealized, abbreviated schematic representation intended to illustrate the basic concept at the heart of the claimed invention.
Figure 2B:
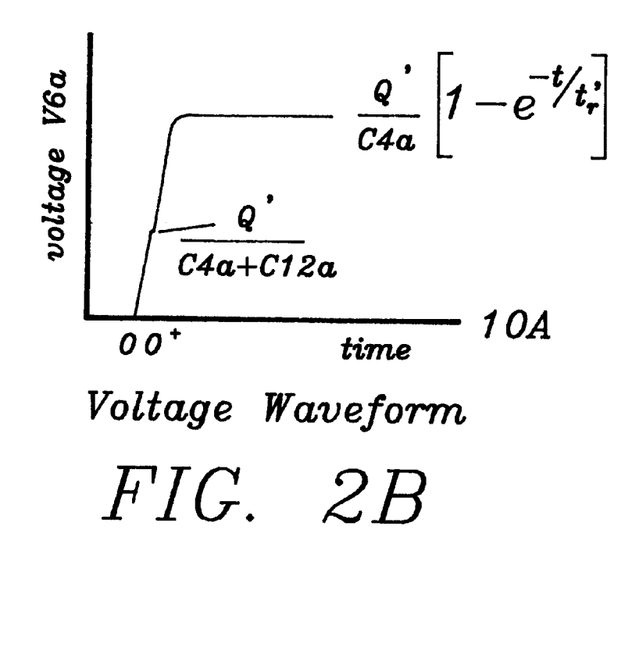

Since amplifier 3a is specified to have zero output impedance (referred to circuit common 8), the initial voltage V7a, due to current from source 11a applied to terminal 7a, must be zero. The pulse initially charges capacitors 4a and 12a in parallel producing, in turn, a voltage signal at terminal 6a which is equal to the charge in the pulse, Q', divided by the parallel capacitance (C4a+C12a).

Immediately after time t=0 the potential at terminal 6a is V6a=Q'/(C4a+C12a), while V7a, the potential at terminal 7a, is still zero. This condition cannot be sustained, since the unity-gain, non-inverting amplifier 3a must force a zero potential difference to exist between terminals 6a and 7a by causing a current, designated i (0⁺) to flow around the loop as shown in the schematic of FIGS. 2(A–B) Zero potential difference means that no charge remains in capacitor 12a: Current i (0⁺) flows until all of the initial charge in capacitor 12a is removed.

This signal-pulse, V6a, shown as waveform 10A is approximated by the mathematical expression (referenced to time t=0):

$$V6a = [Q'/C4a][1 - e^{-t/t_r'}]$$

where: Q'/C4 is the pulse amplitude $t_r'$ is the pulse "rise-time" defined by the charge-collection time-constant of the transducer and the bandwidth of amplifier 3a However, none of the current i (0⁺) enters the amplifier input since amplifier 3a is specified to have infinite input impedance. Thus all of the charge removed from 12a must be deposited in capacitor 4a. After a brief time, capacitor 4a will hold all the charge produced by the original transducer pulse. The voltage across 4a is Q'/C4a, which is the charge in the pulse divided by the value of the integrating capacitor. Since amplifier 3a has unity gain, this voltage will consequently appear at terminal 7a.

Idealized Model (B)

The simplified model shown in FIGS. 2(A–B) is intended only to illustrate the underlying idea of how a unity-gain, non-inverting amplifier can perform the function of a chargeintegrating preamplifier. A more realistic model, shown in FIGS. 2(C–D), is the same (all component values are the same) as that of FIGS. 2(A–B) except for the addition of dischargecomponent 5b connected in parallel with capacitor 4b. In this model, 5b is a resistor (whose resistance is denoted R5b). The parallel combination of capacitor 4b and resistor 5b is connected from input terminal 6b to signal common 8. Resistor 5h typically has very high resistance—tens to hundreds of megohms or more. In the absence of 5b the voltage across capacitor 4b would keep increasing with each impulse of current produced by the transducer. Component 5b provides a means for removing accumulated charge from capacitor 4b so as to insure that the voltage does not build up indefinitely over time, since that would cause eventual saturation and circuit malfunction.

Figure 2C:
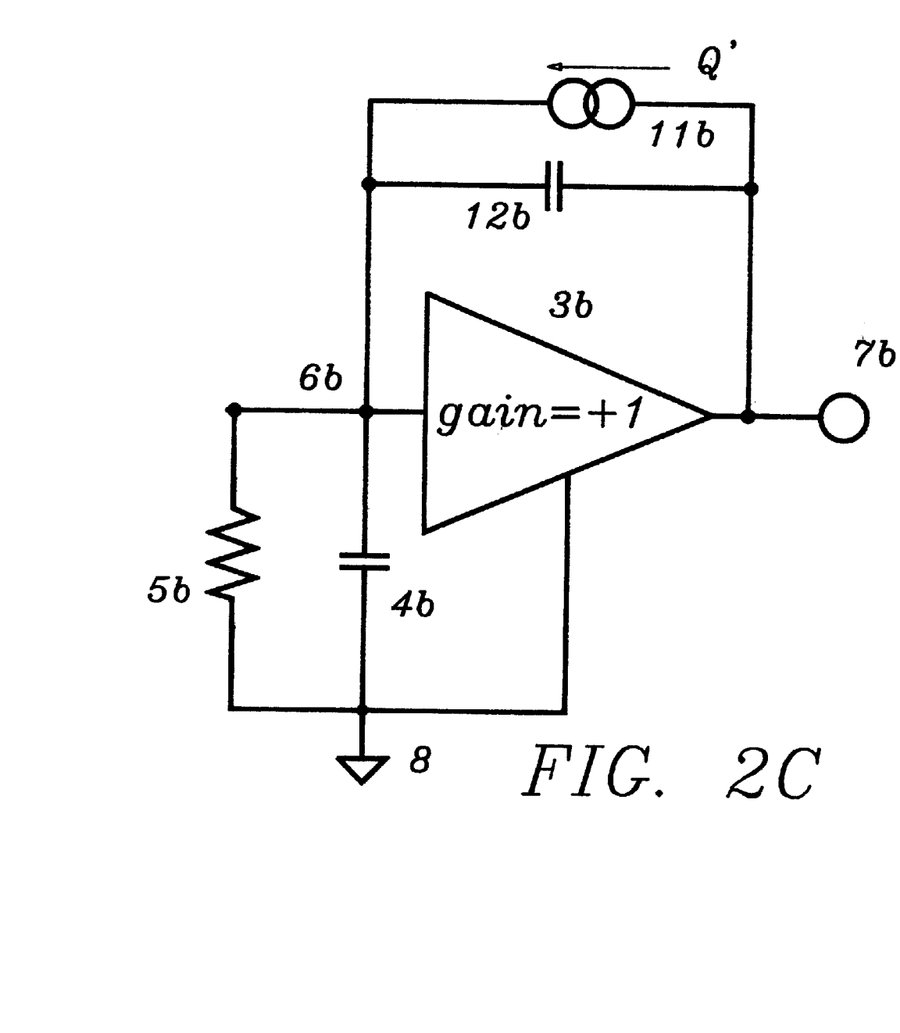
FIG. 2C and 2D are idealized schematic representation incorporating a discharging resistor.
Figure 2D:
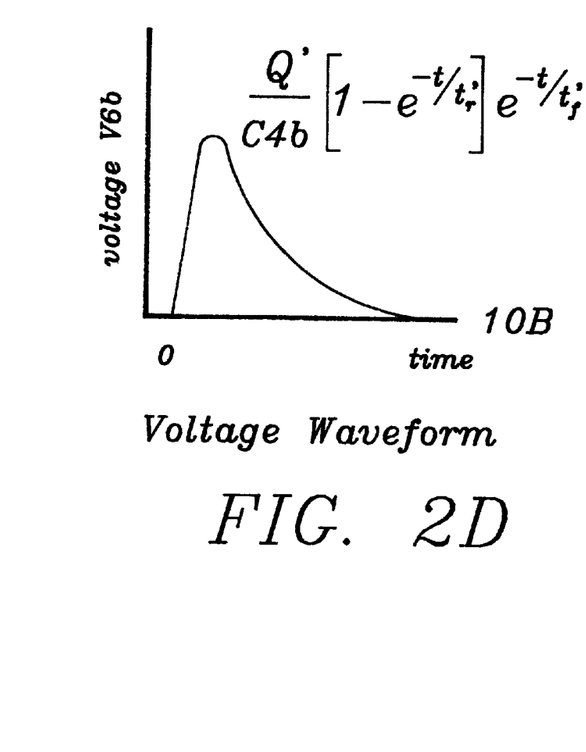

By the action of unity-gain, non-inverting amplifier 3b, the voltage signal-pulse at terminal 6b is reproduced at terminal 7b. This signal-pulse is approximated by the mathematical expression (referenced to time t=0):

$$V6b = [Q'/C4b][1 - e^{-t/t_r'}][e^{-t/t_f'}]$$

where: Q'/C4b is the pulse amplitude $t_r'$ is the pulse "rise-time" defined by the charge-collection time-constant of the transducer and the bandwidth of amplifier 3b and—

$t_f'$ is the pulse "fall-time" defined by the time-constant $t_f' = R5b \times C4b$ Those skilled in the art will recognize that the high-impedance capacitive transducer in FIGS. 2(C–D) is connected to the idealized, unity-gain, non-inverting amplifier 3b in a "bootstrap" configuration. What has not been recognized heretofore is the essential role of capacitor 4b which, in other applications is considered to be a parasitic, or undesired, element, causing degradation of circuit bandwidth, etc. In this application, however, capacitor 4b serves the function of an integrating capacitor—an essential element which defines the amplifier stagegain in a new and novel configuration for a charge-integrating preamplifier.

For a given charge Q', integrating capacitance C4b, and discharge resistor value R5b, the voltage signal pulse at the output of the idealized model of FIGS. 2(C–D) is identical to that of a preamplifier (with equal value integrating capacitor and discharge resistor) of the prior art shown in FIGS. 1(A–B). However, unlike the preamplifier of the prior art, this configuration does not utilize an inverting, high-gain amplifying device. It uses, instead, a much simpler amplifying device; one that is non-inverting and whose gain is unity.

Description of the Invention—Practical Embodiment

The performance of the idealized conceptual model of FIGS. 2(C–D) is incorporated in a practical embodiment; an apparatus for detecting and amplifying weak impulses of energy absorbed from X-rays, gamma-rays, or nuclear charged-particles. The apparatus comprises a detector probe assembly and a signal-receiver assembly, connected together by means of a shielded cable as shown in the schematic diagram of FIG. 3.

Figure 3:
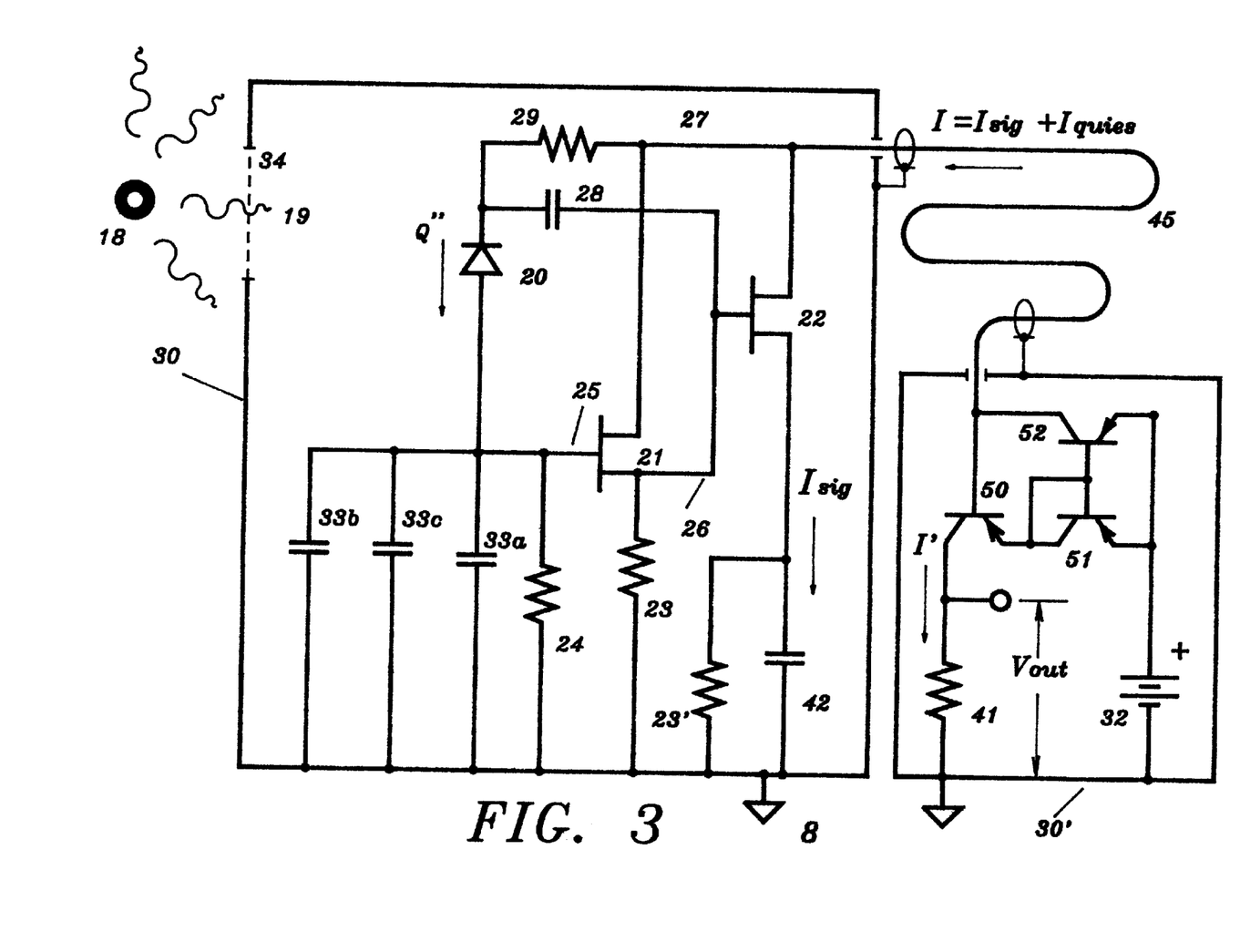
FIG. 3 is a schematic diagram showing a simple, practical embodiment of the invention.

As a practical matter, the circuitry comprising the detector probe assembly is housed in an opaque, metallic enclosure 30 to provide shielding against unwanted ambient light and stray electromagnetic fields. A thin metallic membrane 34 keeps out unwanted light and electromagnetic fields, but allows X-ray photons, gamma-ray photons, or charged particles to impinge on the transducer.

Radioactive source 18 emits energetic gamma ray photons 19, some of which penetrate membrane 34 and strike the transducer, diode 20, which converts the energy of impact into impulses of current. One particular impulse of current is shown which contains a quantity of charge Q" corresponding to the energy deposited by the incident photon.

Diode 20 is back-biased. The cathode is connected through resistor 29 to the power supply bus 27, and is also connected through coupling capacitor 28 to the source terminal of voltage-amplifying device 21. The drain terminals of devices 21 and 22 are connected to power supply bus 27.

Since the amplifier's input-impedance must be very high, and bias and leakage current must be very low—essentially zero—devices 21 and 22 are field-effect transistors, exemplified here as high-frequency, low-noise, N-channel silicon junction field-effect transistors (JFET's) such as the type 2N4416 or its many commercially-available equivalents. Other amplifying devices may be used, but JFET's are preferred for their low-noise characteristics.

Device 21 has transconductance $Gm_{21}$ and is configured as a non-inverting amplifier whose gain, $(V26/V25)= (Gm_{21} \times R23)/(1+Gm_{21} \times R23)$, is just slightly less than unity. The anode of 20 is connected through resistor 24 to signal common, or ground- potential reference point 8. The anode of 20 is also connected to the gate terminal of device 21. Diode 20 is thus coupled (for high-frequency AC or pulse signals) between the output and input (source and gate), respectively, of amplifying device 21.

Resistor 29 provides the bias connection and signal isolation for the cathode of diode 20. The resistance of 29 should be high—1 megohm or more. The capacitance of coupling capacitor 28 must be large relative to the junction capacitance of 20—by at least a factor of ten—in order to provide efficient signal coupling between the cathode of 20 and terminal 26, the source terminal of device 21.

The operating voltage of power supply 32 is in the range 15–24 volts DC, as appropriate for PIN diode transducers and small-signal, low-noise JFET's. Resistor 24 has very high resistance—tens to hundreds of megohms—so as to maintain the high gate-circuit impedance required to sustain satisfactory noise performance. Resistor 24 also functions as a discharging component for the integrating capacitor.

Capacitors 33a, 33b, and 33c comprise the integrating capacitor of the apparatus. They are, respectively, the equivalent input capacitance of device 21, the circuit wiring capacitance, and (if required) a fixed capacitor of predetermined value. These capacitors are connected in parallel between terminal 26, the gate, or input terminal of device 21 and signal common 8. The capacitance of the parallel combination is designated $C_{int}$, to denote "integrating capacitance".

In some circumstances, a fixed capacitor C33c may be utilized to "swamp" the effects of assembly tolerances, component tolerances, etc., thus producing tighter control of overall system gain from unit to unit. If, however, it is desired to achieve the highest possible system gain, then the fixed capacitor, C33c, is omitted from the circuit so as to make $C_{int}$ as small as possible.

Those skilled in the art will recognize the utility of assembling diode 20, devices 21 and 22 and associated circuitry together as a compact unit, maintaining the shortest practical wire length for connections between the terminals of 20 and related components so as to keep wiring capacitance as small as possible.

The source (signal output) terminal of device 21 is connected to the gate (signal input) terminal of device 22. The quiescent DC current for devices 21 and 22 are established by source-bias resistors 23 and 23', respectively. A source-bypass capacitor 42 is connected from the source terminal of device 22 to circuit common, or ground 8.

Device 22 functions as a transconductance amplifier, producing a pulsed current signal $I_{sig}=Gm_{22} \times V26$, where V26 is the voltage signal which appears at terminal 26, and $Gm_{22}$ is the transconductance of device 22. Source-bypass capacitor 42 provides the necessary low-impedance path from the source terminal of device 22 to circuit common, or ground 8 for the fast (high-frequency) leading-edge component of the amplified pulse signals.

In general, the slower, trailing-edge of the signal pulse waveform does not convey any desired information. Fast, narrow pulse signals are preferred as they have less tendency to overlap in time (less "pile-up" in the vocabulary of nuclear counting) and are thus easier to count as separate, distinct pulses. In nuclear-counting applications the pulse trailing-edge is usually attenuated (signal returned to baseline) by "pulse-shaping" techniques which are well-known to those skilled in the art. In particular, we may choose the value of capacitor 42 large enough to efficiently conduct the pulse leading-edge, but small enough to attenuate the slower, trailing-edge (i.e. "high-frequency peaking"). This will enhance the system's overall count-rate capability. In the embodiment shown, the capacitance of 42 is of the order of 1000–10,000 picofarads.

Note that there is no voltage-signal output-terminal associated with the detector probe circuitry contained in shielded enclosure 30. Instead, the amplified pulse-current signal(s) $I_{sig}$ are transmitted via power supply bus 27 through shielded cable 45 to a signal-receiving circuit comprising components 50, 51, 52, and 41.

Quiescent current and amplifier risetime

The quiescent operating current $I_{qules}$ is chosen in accordance with the apparatus' intended application: The leading-edge pulse risetime $t_r$ is a fimction of the gain-bandwidth product of the JFET amplifying devices which, in turn, is strongly influenced by the device quiescent operating current. For commonly-available, small-signal JFET's operating at a quiescent current of 10–20 $\mu A$ the device gain-bandwidth product is relatively low, producing an amplifier pulse risetime of 1–2 $\mu sec$. At a quiescent current of 50–100 $\mu A$ the pulse risetime is of the order of of a few hundreds of nanoseconds. A quiescent current=0.5–1 mA is sufficient to produce the device's maximum gain-bandwidth product which, in turn, produces an amplifier pulse risetime response on the order of a few tens of nanoseconds.

A slower leading-edge risetime response may be entirely acceptable in situations where the photon flux and consequent pulse count-rate is relatively low—on the order of $10^5$ per second or less—particularly when low power consumption is an over-riding consideration as in portable, battery-operated applications.

A faster leading-edge rise-time response is required, however, in situations where the expected photon flux and consequent pulse count-rate is relatively high—on the order of $10^6$ per second and more—and where the lowest possible power consumption is not so important, as in process-monitoring of chemical-laboratory radio-pharmaceutical synthesis procedures.

In the embodiment shown in FIG. 3, resistors 23 and 23' are 100K and 10K ohms, respectively, producing quiescent current of approximately 40 $\mu A$ in device 21 and approximately 800 $\mu A$ in device 22. Those skilled in the art will know how to construct variations on the amplifier bias scheme and how to choose other JFET source-resistor values so as to effect a device quiescent current appropriate for the application at hand.

Stacked, Double-Cascode preamplifier: An
Improved, High-Gain, Low-Noise Embodiment for
use with Large-Area, High-Capacitance Transducers The relatively simple embodiment of FIG. 3 functions well in many applications, particularly those requiring the lowest-power and most compact implementation. However, other, more technically demanding applications, such as high-sensitivity, precision gamma-ray spectroscopy, require performance superior to that offered by the former embodiment. These precision applications require high gain coupled with the lowest possible noise from the detector preamplifier.

Signal levels are almost always weak relative to the noise in the system, particularly when employing indirect-detection of photons via a scintillating crystal. To give some perspective on signal levels: According to generally-accepted data (Harshaw QS Scintillation Detector Catalog, March, 1992) 0.5 MeV gamma-ray energy deposited in a thallium-activated Cesium Iodide (abbreviated CsI(Tl)) scintillating crystal produces 26,000 photons within the crystal. If we assume (optimistically) 100% optical transmission from the crystal into the diode, followed (again, optimistically) by 100% conversion to electronic charge, then 0.5 MeV in the crystal produces 26,000 electron-hole pairs or $0.833 \times 10^{-14}$ coulombs (8.33 femtocoulombs) of electronic charge in the diode. A typical back-biased PIN silicon diode of area 1 $cm^2$ has a junction capacitance of approximately 50 picofarads: 8.33 femtocoulombs deposited in 50 picofarads produces a voltage pulse of 166 microvolts.

Figure 4:
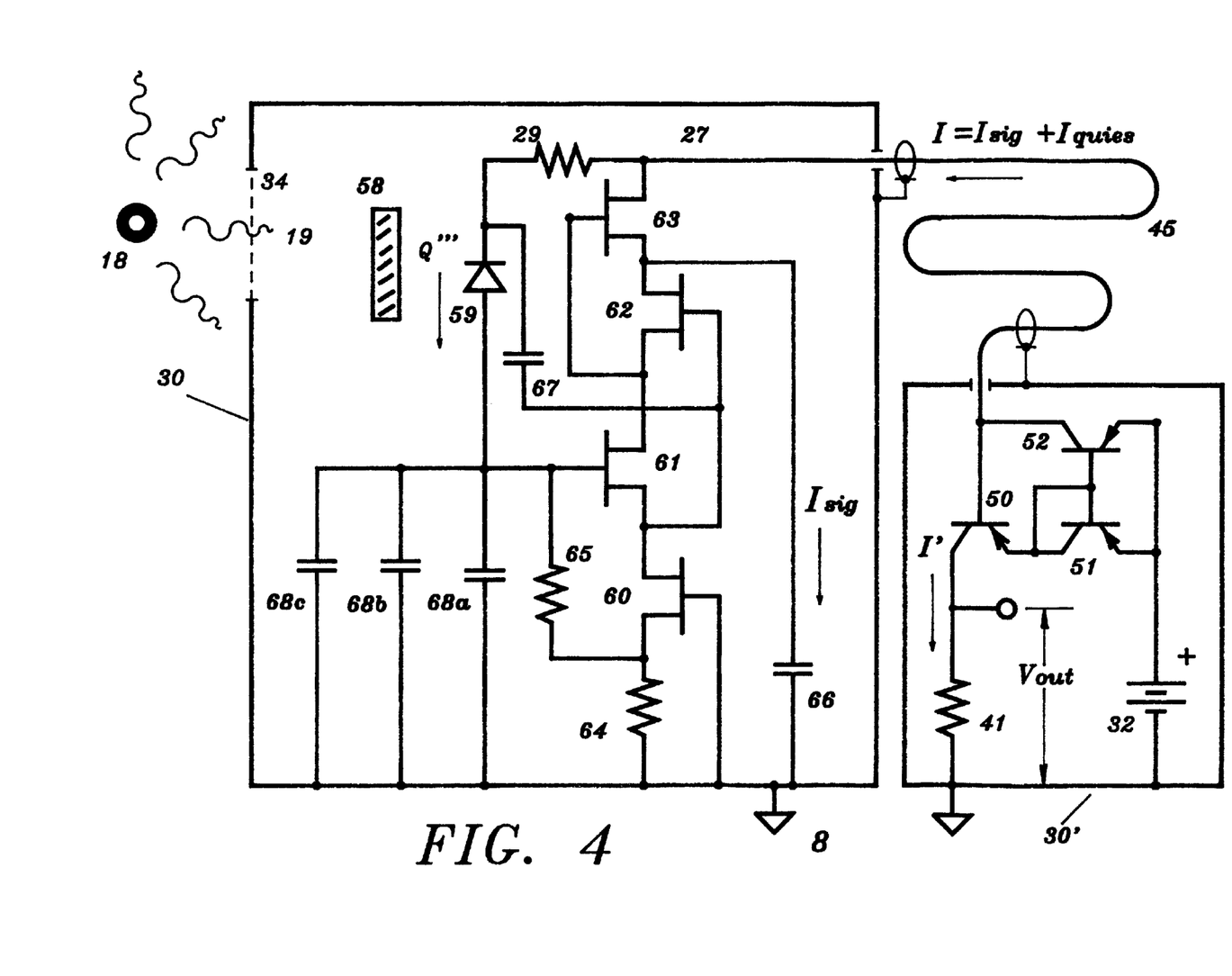
FIG. 4 is a schematic diagram showing an improved, high-gain, low-noise embodiment.

A detector-probe preamplifier configured as in FIG. 4 provides the required high-gain, combined with low noise in order to achieve optimum performance with this type of transducer. The circuit in FIG. 4 employs four amplifying devices, designated 60, 61, 62, 63.

The main amplifying device 61 must have high enough quiescent current to achieve low noise and high-gain, but we wish to keep the overall system quiescent current as low as practical. Thus, rather than employing separate, parallel DC circuit paths for the main amplifying stage and the output current-driver stage (as in FIG. 3), in the embodiment of FIG. 4 all of the amplifying devices in the detector preamplifier circuit are connected in series for DC. As before, the amplifying devices are exemplified as high-gain, high-frequency, low-noise, N-channel junction field-effect transistors. Device 60 is a type 2N4416, or any of several commercial equivalents.

Low-noise performance requires that main-amplifier device 61 be selected as a type whose total interelectrode capacitance (the sum of the gate-to-source capacitance plus gate-to-drain capacitance) is nominally of the same order of magnitude as the junction capacitance of the detector transducer diode, 59. The following stage, device 62, should be a similar type.

For a diode transducer with junction capacitance on the order of 10–15 pF, the 2N4416 (total interelectrode capacitance~5 pF) or equivalent is found to be a satisfactory choice for 61 and 62. For 50 pF transducer capacitance, a high-transconductance, low-noise device such as InterFet Corporation IRF4501, or equivalent, with 35–40 pF total interelectrode capacitance, provides the required overall low noise performance.

The output current-driver stage 63 should also be a relatively high-transconductance device, such as a type IRF4501, a type 2N4857, or equivalent.

Other types of field-effect transistors, such as depletion-mode MOS devices might also be used, particularly if the circuit were to be implemented as a monolithic integrated circuit. However, when implemented using discrete components, N-channel JFET's are preferred—particularly for the main amplifying stage 61, as these devices generally possess the lowest noise.

Device 60 is not used explicitly as a signal-amplifying device; rather, the combination of device 60 and resistor 64 comprises a current source which establishes the quiescent current through the entire preamplifier (since the devices are connected in series for DC ) and which also serves as a high-impedance load for the main amplifying stage 61, helping to insure that the gain of the main amplifying stage (referred to circuit common) is as close to 1,000 (unity) as possible. The gate of device 60 is shown connected directly to circuit common—or ground—potential. The source terminal of 60 is connected to ground through resistor 64. Utilizing the device-manufacturer's published gate-voltage/drain-current characteristics for device 60 the value of resistor 64 is chosen according to standard engineering technique so as to fix device 60 's quiscent current at the desired value. For high-gain and low-noise operation with the amplifying devices exemplified here, the quiescent current is set within the nominal range 0.5–1.0 mA.

As in the embodiment of FIG. 3, transducer diode 59 is back-biased. The anode of 59 is connected to the gate of amplifying device 61. Resistor 29 is connected between the cathode of 59 and the detector probe's+power supply bus 27. In addition to the bias connection, 29 also provides signal isolation. Resistor 29 has high resistance—1 megohm or more. The cathode of 59 is also AC coupled to the source (output) terminal of amplifying device 61 through capacitor 67. For best gain and low-noise performance coupling capacitor 67 must have high capacitance to insure efficient signal-coupling—In this embodiment the capacitance of 67 should be a factor of 100 or more greater than the junction capacitance of 59.

Discharge means

The gate of device 61 is returned to the source of device 60 through discharge means 65. 65 serves to remove accumulated charge in the integrating capacitor Cint=C68a+C68b+C68c as explained previously. In the embodiment shown in FIG. 4 discharge means 65 is a resistor of very high resistance—on the order of 1000 megohms, in order to preserve highest gain and lowest noise performance. The leakage current through diode 59 and the gate junction leakage current of device 61 is typically on the order of 1 nanoampere or less. The resultant voltage drop across 65 plus the DC potential at the source of device 60 established the correct operating gate bias for device 61.

Those skilled in the art will recognize that the discharge means exemplified by 65 may be implemented in other ways, such as another JFET biased to cut-off so as to provide a high-resistance discharge path.

Maximizing Circuit Gain

Impulses of current are generated in capacitive transducer 59 in response to impulses of energy deposited directly in 59 by nuclear charged particles, gamma-ray photons, or x-ray photons, or produced indirectly through the interaction of charged particles, gamma-ray photons, or x-ray photons in an optically-coupled, scintillating crystal, 58.

For an impulse of current with total charge Q''', a voltage signal is produced at the gate of device 61 whose amplitude is equal to $Q'''/C_{int}$. $C_{int}$ is the value of the integrating capacitance which, in turn, is the sum of the effective device interelectrode capacitance C68a associated with the gate of 61, plus the wiring capacitance C68b plus (if required) a fixed capacitance of predetermined valuel, C68c.

Returning for a moment to to the embodiment of FIG. 3: The effective interelectrode capacitance, C33a, is dominated by the gate-to-drain capacitance of amplifying device 21, since the gate-to-source capacitance is largely cancelled by the action of the unity-gain, non-inverting first-amplifier stage. As long as the gate-to-drain capacitance is small (typically less than 1 pF for "small" JFET's), the overall integrating capacitance is small and the system gain remains large. In the embodiment of FIG. 4, we are using (presumably) a larger-area transducer diode, so we must employ high-transconductance FET amplifying devices of relatively large geometry with up to an order of magnitude larger gate-to-drain capacitance leading, in turn, to a correspondingly large increase in total integrating capacitance. This would have the effect of substantially reducing the overall gain of the system were it not for the particular amplifier circuit configuration employed here.

Since amplifying device 61 is a unity-gain, non-inverting amplifier, any voltage signal produced at the gate of 61 is reproduced at its source terminal. Device 62 is also configured as a unity-gain source-follower. Those skilled in the art will recognize that device 62 functions as a "unity-gain, bootstrap amplifier stage" and that amplifying devices 61 and 62 are connected in the well-known "cascode-bootstrap" configuration wherein the gate terminal of 62 is connected to the source terminal of 61, and the source terminal of 62 is conected to the drain terminal of 61. The gate and drain of 61 are therefore held at the same signal potential. In this manner the effect of the gate-to-drain capacitance of device 61 is largely cancelled, considerably enhancing overall system gain.

The cascode bootstrap combination of two amplifying devices 61 and 62 forms, in effect, an equivalent, composite amplifying device with very low output conductance and very low effective gate-to-drain capacitance. This composite device configuration substantially enhances the preamplifier's overall gain and frequency response (reference, Oxner, Siliconix, Inc. *Designing With Field-Effect Transistors*, Second Edition, McGraw-Hill, 1990.

Dutput current-duver Stage

Device 63 produces an output current-signal in response to an input voltage-signal (i.e. device 63 is a transconductance amplifier) and functions as an output current-driver stage. The gate terminal of device 63 is connected to the source terminal of device 62; the source terminal of 63 is connected to the drain terminal of 62. The gate terminal of 62 is connected to the source terminal of 61 and the source terminal of 62 is connected to the drain terminal of 61. Thus, devices 62 - 63, as well as devices 62 - 61 are connected in a cascode configuration. Hence the description, "stacked, double-cascode". The same voltage signal which appears at the gate of 61 is reproduced at the source terminal of 61, and is again reproduced at the souce terminal of 62 and the gate terminal of 63.

In order to conduct the fast, leading-edge component of the output-current signal pulse, the source terminal of output current-driver stage 63 is AC-bypassed to signal common by capacitor 66. Without this bypass capacitor, device 63's source-return path to signal ground would present a very high impedance, substantially reducing the gain of that amplifier stage. Capacitor 66 should have an AC impedance which is low relative to the source-terminal output impedance of 63, but not too low. The correct value for bypass capacitor 66 depends on pulse-shaping and timing requirements. Too small a capacitance (too high an impedance), of course, limits the gain of the amplifying stage. Too large a capacitance (too low an impedance) allows a long-duration trailing edge on the output pulse, which does not convey useful information and which may, in fact, contribute to unwanted pulse overlap or "pile-up". A capacitance value in the range of 0.001 to 0.01 uF has been found to be correct for fast pulses from direct detection of x-rays and gamma rays in the diode, while 0.01 to 0.1 uF has been found to be correct when the diode is coupled with a relatively slow scintillator such as CsI(Tl).

The drain of device 63 is connected to the + power supply bus 27. The output-signal current-pulses are transmitted via power supply bus 27 through shielded cable 45 to a signal receiving circuit comprising components 50, 51, 52, and 41.

Signal-Receiving Circuit

As a practical matter, the signal-receiving circuit and subsequent amplifying stages (subsequent amplifying stages are not shown here, as they follow standard design practice) are enclosed in a metallic enclosure 30' which is connected to circuit common or ground potential 8 and provides shielding against unwanted electronic noise and electromagnetic fields.

In the embodiment shown, the signal-receiving circuit comprises low-noise, small-signal, PNP bipolar junction transistors 50, 51, 52 and load resistor 41. The input impedance of this signal-receiving circuit, expressed in units of ohms, is:

Input Impedance (ohms)=$50/I_{qules}$ (mA.)

Thus, for a current of $I_{qules}$=1.0 mA in coaxial cable 45, the signal-receiving circuit input impedance is 50 ohms, which matches the characteristic impedance of commonly-used varieties of coaxial cable. A matched cable termination, in turn, allows the interconnecting cable 45 to be of arbitrary length, while maintaining optimum pulse fidelity in applications involving high pulse count rates and fast leading-edge risetimes.

The signal-receiving circuit shown in this embodiment is known to those skilled in the art as a "Wilson Current Mirror" configuration, wherein the total current $I=I_{sig}+I_{qules}$ in cable 45 is reproduced or "mirrored" (I=I') in resistor 41. The circuit comprising transistors 50, 51, 52, and resistor 41 constitutes a simple but effective transimpedance amplifier whose gain, expressed in units of ohms, is just the resistance of 41, designated R41. Thus, an amplified signal voltage-pulse $V_{out}$ is expressed across resistor 41. The overall system gain is proportional to the transconductance of the output current-driver stage, and inversely proportional to the integrating capacitance. For the embodiment shown in FIG. 3 the overall system gain, expressed in units of "volts out per unit transducer charge" is given by $V_{out}/Q"=Gm_{22} \times R41/C_{int}$.

In addition to providing the desired low-input impedance the Wilson Current MirTor circuit configuration provides the required bandwidth and substantial rejection of hum, noise, and other perturbing signals which may be present at the output of power supply 32. However, those skilled in the art will recognize that, with suitable circuit modifications, other transimpedance amplifier configurations, such as a common-base bipolar junction transistor amplifier, an inverting feedback amplifier, etc. can be made to perform in a manner equivalent to the signal-receiving circuit described here.

Numerical Example

As a practical, illustrative example of the performance of the apparatus shown in FIG. 3, suppose 60 keV gamma-ray photons are fully absorbed in a silicon PIN diode transducer. Since 3.6 electron volts are required to liberate each holeelectron pair in silicon, the amount of charge generated by each photon impact is:

$$Q = (2 \times 60{,}000/3.6) \times (1.6 \times 10^{-19}) = 5.34 \times 10^{-15} \text{ coulombs}$$

Practical values for circuit parameters in the detector probe and signal-receiving circuit are as allows:

$Gm_{22} = 0.0035$ siemens
$C_{int} = 1.5 \times 10^{-12}$ farad
$R41 = 10{,}000$ ohms Thus, the signal pulse-amplitude, $V_{out}$ appearing across R41 is:

$$V_{out} = 5.34 \times 10^{-15} \times 0.0035 \times 10{,}000 / 1.5 \times 10^{-12} = 0.124 \text{ volts}$$

Summary, Ramifications, and Scope of the Invention

A simple, compact, stable, wide-band, low-noise, inexpensive, low-power non-inverting amplifier with unity gain is easily fabricated utilizing only a few components. This is the heart of a novel charge-integrating preamplifier. A detector probe assembly incorporating such a unity-gain amplifier in conjunction with an appropriate transducer, an integrating capacitor, and a transconductance amplifier, in combination with a remotely-located signal receiver, comprises a useful apparatus for detecting and amplifying impulses of absorbed energy from X-ray or gamma-ray photons, or nuclear charged particles.

Applications such as portable, battery-powered radiation survey instrumentation, miniature sensors for monitoring and feedback in radiation chemistry process-control, and other applications, are well-served. The apparatus described is particularly well-suited to applications requiring miniature radiation probes located far from subsequent amplifying stages.

The above description illustrates a particular application relating to X-ray, gamma-ray or nuclear charged-particle detection. Utilizing a suitable transducer, other applications, such as thermal, visible, and acoustic energy detection and measurement are also served by the invention. While the above description contains many specifications, these should not be construed as limitations on the scope of the invention, but rather as an examples of preferred embodiments. Other variations are possible, and may be utilized according to the particular application. Accordingly, the scope of the invention should be determined not by the embodiments illustrated, but by the appended claims and their legal equivalents.

I claim:

1. An apparatus for detecting and amplifying impulses of energy absorbed from incident nuclear-charged particles, X-ray photons, or gamma-ray photons, the apparatus comprising a detector-probe assembly and a signal-receiving assembly, said detector-probe assembly comprising a high-impedance capacitive transducer for converting impulses of energy absorbed from charged-particles, X-ray photons, or gammaray photons incident on the transducer into corresponding impulses of electronic current, a non-inverting first voltage-amplifying stage having a signal input, a signal output, and a signal common, or ground-reference point, wherein the voltage gain of the first voltage-amplifying stage, referred to signal common, is essentially unity, an integrating capacitor comprising a parallel combination of components, including wiring capacitance and the equivalent input capacitance of said first voltage-amplifying stage, said integrating capacitor connected between the input of said first voltage amplifying stage and signal common, said integrating capacitor connected to a discharge means for removing accumulated charge from said integrating capacitor, said high-impedance capacitive transducer being ac-coupled between output and input of said first voltage-amplifying stage, a transconductance amplifier stage having a voltage input and a current output, where said voltage input is connected to the signal-output of the first voltage-amplifying stage, and said current output is connected to the input stage of the signal-receiving assembly through a shielded cable, the input stage of the signal-receiving assembly comprising a transimpedance amplifier.

2. The apparatus of claim 1 in which said non-inverting first voltage-amplifiing stage is implemented as a cascode-bootstrap circuit comprising a first field-effect transistor main amplifier stage plus a second field-effect transistor unity-gain bootstrap amplifier stage, wherein the source terminal of the the first field-effect transistor is connected to the gate terminal of the second field-effect transistor, and the source terminal of the second field-effect transistor is connected to the drain terminal of the first field-effect transistor.

3. The apparatus of claim 1 wherein said non-inverting first voltage-amplifyg stage, together with said transconductance amplifier stage, are implemented as a stacked, double-cascode circuit comprising a first field-effect transistor main amplifying stage, a second field-effect transistor unity-gain bootstrap-amplifier stage, and a third field-effect transistor transconductance amplifier stage, wherein the source terminal of the first field-effect transistor is connected to the gate terminal of the second field-effect transistor, the source terminal of the second field-effect transistor is connected to the drain terminal of the first field-effect transistor and to the gate terminal of the third field-effect transistor, the source terminal of the third field-effect transistor is connected to the drain terminal of the second field-effect transistor, and the source terminal of the third field-effect transistor being AC-bypassed to signal common by means of a capacitor of predetermined value.

4. An apparatus for detecting and amplifying impulses of energy absorbed from incident nuclear-charged particles, X-ray photons, or gamma-ray photons, said apparatus comprising a detector-probe assembly and a signal-receiving assembly, said detector-probe assembly comprising a high-impedance capacitive transducer for converting impulses of energy absorbed from charged-particles, X-ray photons, or gammaray photons incident on said transducer into corresponding impulses of electronic current, a first junction field-effect transistor stage having a signal-input gate terminal, a signal-output source terminal, and a signal common, or groundreference point, wherein the voltage gain from signal-input gate to signal-output source of the first junction field-effect transistor stage, referred to signal common, is essentially unity and non-inverting, an integrating capacitor comprising a parallel combination of components, including wiring capacitance and the equivalent input capacitance of the first junction field-effect transistor stage, said integrating capacitor connected between the signal-input gate of the first junction field-effect transistor stage and signal common, said integrating capacitor connected to a discharge means for removing accumulated charge from said integrating capacitor, said transducer being AC-coupled between signal-output source terminal and signal-input gate terminal of the first junction field-effect transistor stage, a second junction field-effect transistor transconductance amplifier stage, having a voltage-input gate terminal, a source terminal, and a current-output drain terminal, where the voltage-input gate terminal of the second junction field-effect transistor stage is connected to the source terminal of the first junction field-effect transistor stage, the drain terminal of the second junction field-effect transistor stage is connected to the input stage of the signal receiving assembly through a shielded cable, said input stage of the signal-receiving assembly comprising a transimpedance amplifier.

5. The apparatus of claim 4 in which said transducer is a back-biased semiconductor diode.

6. The apparatus of claim 4 in which said transducer comprises a back-biased semiconductor diode optically-coupled to a scintillating crystal.

7. The apparatus of claim 4 in which said shielded cable is a single-conductor, coaxial cable which carries both power to, and signal from, said detector-probe assembly.

8. The apparatus of claim 4 in which the input impedance of the transimpedance amplifier in the signal-receiving assembly is matched to the characteristic impedance of the interconnecting cable.

* * * * *

UNITED STATES PATENT AND TRADEMARK OFFICE
CERTIFICATE OF CORRECTION

PATENT NO.   : 6,054,705
DATED        : April 25, 2000
INVENTOR(S)  : Lewis Carroll It is certified that error appears in the above-identified patent and that said Letters Patent is hereby corrected as shown below:

Column 5,
Line 2, "...a *ftlndamental* concept..." should be changed to -- ...a *fundamental* concept... --
Line 41, "...the *bandwvidth* of..." should be changed to -- ...the *bandwidth* of... --
Line 56, "...*chargeintegrating*..." should be changed to -- ...*charge-integrating*... --
Line 59, "...*dischargecomponent*..." should be changed to separate, distinct words -- ...*discharge component*... --.

The following seven items were first covered in Amendment D of our original CIP application # 08/726,849 which was submitted just prior to assignment of a new CIP application number 08/834,089. Application #08/726,849 was subsequently abandoned, but Amendment D was never incorporated in the "daughter" application.

Column 9,
Line 17, "$0.833 \times 10^{-14}$ coulombs (8.33 femtocoulombs)" is incorrect and should be changed to -- $0.416 \times 10^{-14}$ coulombs (4.16 femtocoulombs) --.
Line 20, "8.33 femtocoulombs" is incorrect and should be changed to -- 4.16 femtocoulombs --.
Line 21, "166 microvolts" is incorrect and should be changed to -- 83 microvolts --.

Column 11,
Line 8, "up to an order of magnitude..." is incorrect and should be changed to -- more than order of magnitude ... --
Line 35, there is a missing parenthesis. Please add a closing parenthesis as follows: -- ...McGraw-Hill, 1990) --.

Column 13,
Line 3, "$Q = (2 \times 60{,}000 / 3.6) \times (1.6 \times 10^{-19}) = 5.34 \times 10^{-15}$ coulombs" is incorrect and should be changed to -- $Q = (60{,}000 / 3.6) \times (1.6 \times 10^{-19}) = 2.67 \times 10^{-15}$ coulombs --.

UNITED STATES PATENT AND TRADEMARK OFFICE
CERTIFICATE OF CORRECTION

PATENT NO. : 6,054,705
DATED : April 25, 2000
INVENTOR(S) : Lewis Carroll

It is certified that error appears in the above-identified patent and that said Letters Patent is hereby corrected as shown below:

<u>Column 13 contd.</u>
Line 13, "$V_{out} = 5.34 \times 10^{-15} \times .0035 \times 10,000 / 1.5 \times 10^{-12} = 0.124$ volts" is incorrect and should be changed to -- $V_{out} = 2.65 \times 10^{-15} \times .0035 \times 10,000 / 1.5 \times 10^{-12} = 0.062$ volts --.

Signed and Sealed this

Twenty-third Day of October, 2001

*Attest:*

*Attesting Officer*

NICHOLAS P. GODICI
*Acting Director of the United States Patent and Trademark Office*